(12) United States Patent
Moretti

(10) Patent No.: US 9,000,226 B2
(45) Date of Patent: Apr. 7, 2015

(54) ALDEHYDES AS PERFUMING INGREDIENTS

(71) Applicant: Firmenich SA, Geneva (CH)

(72) Inventor: Robert Moretti, Geneva (CH)

(73) Assignee: Firmenich SA, Geneva (CH)

( * ) Notice: Subject to any disclaimer, the term of this patent is extended or adjusted under 35 U.S.C. 154(b) by 0 days.

(21) Appl. No.: 14/376,972

(22) PCT Filed: Jan. 24, 2013

(86) PCT No.: PCT/EP2013/051274
§ 371 (c)(1),
(2) Date: Aug. 6, 2014

(87) PCT Pub. No.: WO2013/117433
PCT Pub. Date: Aug. 15, 2013

(65) Prior Publication Data
US 2015/0051133 A1 Feb. 19, 2015

(30) Foreign Application Priority Data
Feb. 9, 2012 (EP) .................... 12154700

(51) Int. Cl.
*C07C 47/11* (2006.01)
*C07C 47/225* (2006.01)
*C07C 47/115* (2006.01)
*C11B 9/00* (2006.01)

(52) U.S. Cl.
CPC .............. *C07C 47/11* (2013.01); *C07C 47/225* (2013.01); *C07C 47/115* (2013.01); *C11B 9/0034* (2013.01); *C11B 9/0046* (2013.01); *C11B 9/003* (2013.01); *C07C 2101/14* (2013.01); *C07C 2101/16* (2013.01); *C07C 2102/42* (2013.01); *C07C 2101/08* (2013.01)

(58) Field of Classification Search
CPC ....................................... C07C 47/11

USPC ............................................. 568/446; 512/22
See application file for complete search history.

(56) References Cited

U.S. PATENT DOCUMENTS

| 6,172,016 B1 | 1/2001 | Pagano et al. | |
| 8,815,792 B2 * | 8/2014 | Moretti | 512/20 |
| 8,871,982 B2 * | 10/2014 | Saudan et al. | 568/434 |

FOREIGN PATENT DOCUMENTS

| EP | 1 054 053 A2 | 11/2000 |
| EP | 1 067 118 A1 | 1/2001 |
| WO | 2010/052635 A1 | 5/2010 |
| WO | WO 2012/150053 A1 * | 11/2012 |

OTHER PUBLICATIONS

International Search Report and Written Opinion, Application No. PCT/EP2013/051274, Apr. 24, 2013.

* cited by examiner

*Primary Examiner* — John Hardee
(74) *Attorney, Agent, or Firm* — Winston & Strawn LLP

(57) ABSTRACT

An aldehyde of formula (I)

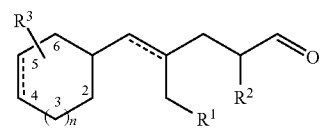

in the form of any one of its stereoisomers or a mixture thereof, wherein each dotted line, independently from each other, represents a single or double bond; n is 0 or 1; $R^1$ is a hydrogen atom or a methyl group; $R^2$ is a hydrogen atom or a methyl or ethyl group; and $R^3$, which can be present in any of positions 2 to 6 of the cyclic moiety, is a hydrogen atom or a methyl or ethyl group, or a $CH_2$ group bridging positions 3 and 6. Also, the use of the aldehyde as perfuming ingredient to impart odor notes of the aldehyde, lily of the valley type.

16 Claims, No Drawings

ALDEHYDES AS PERFUMING INGREDIENTS

CROSS-REFERENCE TO RELATED APPLICATIONS

This application is a 371 filing of International Patent Application PCT/EP2013/051274 filed Jan. 24, 2013, which claims priority to European application no. 12154700.4 filed Feb. 9, 2012.

TECHNICAL FIELD

The present invention relates to the field of perfumery. More particularly, it concerns an aldehyde of formula (I) as defined further below and its use in perfumery as perfuming ingredient. Therefore, following what is mentioned herein, the present invention comprises the invention's compound as part of a perfuming composition or of a perfuming consumer product.

PRIOR ART

To the best of our knowledge, none of the invention's compounds is known.

The structurally closest analogues being known as perfuming ingredients are reported in EP 1067118 and U.S. Pat. No. 6,172,016. However, this prior art document does not report or suggest any organoleptic properties of the compounds of formula (I), or any use of said compounds in the field of perfumery. Furthermore, said prior art document reports compounds having organoleptic properties significantly different.

DESCRIPTION OF THE INVENTION

We have now surprisingly discovered that a compound of formula

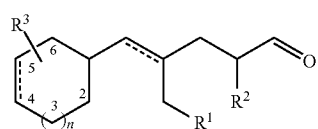

(I)

in the form of any one of its stereoisomers or a mixture thereof, and wherein each dotted line, independently from each other, represents a single or double bond;
n is 0 or 1;
$R^1$ represents a hydrogen atom or a methyl group;
$R^2$ represents a hydrogen atom or a methyl or ethyl group; and
$R^3$, which is a substituent in any of the positions 2 to 6 of the cyclic moiety, represents a hydrogen atom or a methyl or ethyl group, or a $CH_2$ group bridging positions 3 and 6;
can be used as perfuming ingredient, for instance to impart odor notes of the aldehyde, lily of the valley type.

For the sake of clarity, by the expression "any one of its stereoisomers", or the similar, it is meant the normal meaning understood by a person skilled in the art, i.e. that the invention's compound can be a pure enantiomer (if chiral) or diastereomer (e.g. the double bond is in a conformation E or Z).

For the sake of clarity, by the expression "wherein one dotted line represents a carbon-carbon single bond and the other a carbon-carbon single or double bond", or the similar, it is meant the normal meaning understood by a person skilled in the art, i.e. that the whole bonding (solid and dotted lines) between the carbon atoms connected by said dotted line is a carbon-carbon single or double bond.

According to a particular embodiment of the invention, n is 1.

According to any one of the above embodiments of the invention, $R^3$ represents a hydrogen atom or a methyl group, or a $CH_2$ group bridging positions 3 and 6 of the cyclic moiety.

According to a particular embodiment of the invention, compound (I) is of formula

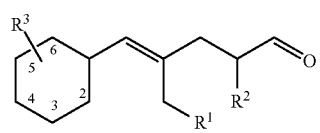

(II)

wherein $R^1$ represents a hydrogen atom or a methyl group; $R^2$ represents a hydrogen atom or a methyl or ethyl group; and $R^3$ represents a hydrogen atom or a methyl group, or a $CH_2$ group bridging positions 3 and 6 of the cyclic moiety; provided that at least one of $R^2$ and $R^3$ is a hydrogen atom.

According to any one of the above embodiments of the invention, said compounds (I) are $C_{12}$-$C_{13}$ compounds.

As mentioned above, the present invention's compound can be in the form of a mixture of isomers of configuration E or Z (in particular concerning the carbon-carbon double bond in the acyclic moiety). According to any one of the above embodiments of the invention, said compounds (I) (when having a double bond in the acyclic moiety) or (II) is in the form of a mixture of isomers having a E/Z ratio of at least 60/40, or even of at least 80/20.

As specific examples of the invention's compounds, one may cite, as non-limiting example, (E)-5-cyclohexyl-2,4-dimethylpent-4-enal, which possesses a strong aldehyde, floral, lily of the valley odor, reminding of the odor of 3-(4-tert-butyl-1-cyclohexen-1-yl)propanal (see EP1054053), with phenolic bottom notes.

As other example, one may cite (E)-5-cyclohexyl-4-methylpent-4-enal, which possesses a clean aldehyde, green, lily of the valley odor, with a fatty connotation.

As other specific, but non-limiting, examples of the invention's compounds, one may cite the following ones in Table 1:

TABLE 1

Invention's compounds and their odor properties

| Compound structure and name | Odor notes |
| --- | --- |
| ![structure] (E)-4-methyl-5-(4-methylcyclohexyl)pent-4-enal | Aldehyde, lily of the valley, dry and flowery |

TABLE 1-continued

| Invention's compounds and their odor properties | |
|---|---|
| Compound structure and name | Odor notes |
| 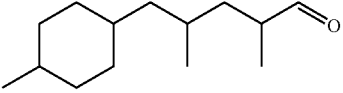<br>2,4-dimethyl-5-(4-methylcyclohexyl)pentanal | Aldehyde, lily of the valley, slightly milky |
| 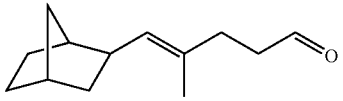<br>5-(bicyclo[2.2.1]heptan-2-yl)-4-methylpent-4-enal | Aldehyde, lily of the valley, decenal |
| 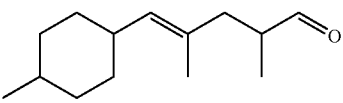<br>(E)-2,4-dimethyl-5-(4-methylcyclohexyl)pent-4-enal | Aldehyde, lily of the valley, reminding of 3-(4-methyl-3-pentenyl)-3-cyclohexene-1-carbaldehyde |
| 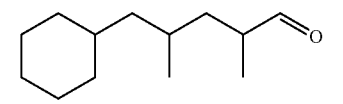<br>5-cyclohexyl-2,4-dimethylpentanal | Aldehyde, lily of the valley, with green and watery aspect of the lily of the valley |
| 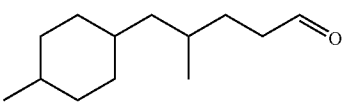<br>4-methyl-5-(4-methylcyclohexyl)pentanal | Aldehyde, lily of the valley, slightly 2-methylundecanal |
| 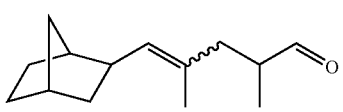<br>5-((1RS,4SR)-bicyclo[2.2.1]heptan-2-yl)-2,4-dimethylpent-4-enal | Aldehyde, lily of the valley, nice |
| 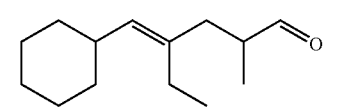<br>4-(cyclohexylmethylene)-2-methylhexanal | Aldehyde, lily of the valley |
| 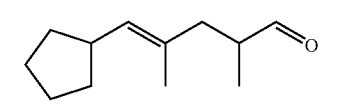<br>5-cyclopentyl-2,4-dimethylpent-4-enal | Aldehyde, lily of the valley, reminding of cyclamen |
| 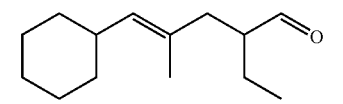<br>(E)-5-cyclohexyl-2-ethyl-4-methylpent-4-enal | Aldehyde, lily of the valley, mimosa, slightly citrusy |
| 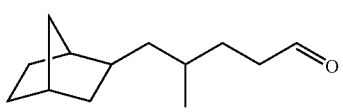<br>5-((1RS,2RS,4SR)-bicyclo[2.2.1]heptan-2-yl)-4-methylpentanal | Aldehyde, lily of the valley, dry, nice |

TABLE 1-continued

Invention's compounds and their odor properties

| Compound structure and name | Odor notes |
|---|---|
| 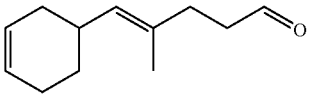<br>(E)-5-(cyclohex-3-enyl)-4-methylpent-4-enal | Aldehyde, lily of the valley, slightly ozone |

According to a particular embodiment of the invention, the compounds of formula (I) are (E)-5-cyclohexyl-2,4-dimethylpent-4-enal, (E)-5-cyclohexyl-4-methylpent-4-enal, 5-((1RS,2RS,4SR)-bicyclo[2.2.1]heptan-2-yl)-4-methylpentanal, 5-((1RS,4SR)-bicyclo[2.2.1]heptan-2-yl)-2,4-dimethylpent-4-enal or 5-cyclohexyl-2,4-dimethylpentanal.

When the odor of the invention's compounds is compared with that of the prior art structural analogues, then the invention's compounds distinguish themselves by lacking, or not possessing a significant, the ylang, woody and/or rosy notes so characteristic of the to prior art compound(s). Said differences lend the invention's compounds and the prior art compounds to be each suitable for different uses, i.e. to impart different organoleptic impressions.

The compounds according to the invention are also novel and therefore an object of the invention.

As mentioned above, the invention concerns the use of a compound of formula (I) as perfuming ingredient. In other words, it concerns a method to confer, enhance, improve or modify the odor properties of a perfuming composition or of a perfumed article, which method comprises adding to said composition or article an effective amount of at least a compound of formula (I). By "use of a compound of formula (I)" it has to be understood here also the use of any compositions containing a compound (I) and which can be advantageously employed in perfumery industry.

Said compositions, which in fact can be advantageously employed as perfuming ingredients, are also an object of the present invention.

Therefore, another object of the present invention is a perfuming composition comprising:
i) as perfuming ingredient, at least one invention's compound as defined above;
ii) at least one ingredient selected from the group consisting of a perfumery carrier and a perfumery base; and
iii) optionally at least one perfumery adjuvant.

By "perfumery carrier" we mean here a material which is practically neutral from a perfumery point of view, i.e. that does not significantly alter the organoleptic properties of perfuming ingredients. Said carrier may be a liquid or a solid.

As liquid carrier one may cite, as non-limiting examples, an emulsifying system, i.e. a solvent and a surfactant system, or a solvent commonly used in perfumery. A detailed description of the nature and type of solvents commonly used in perfumery cannot be exhaustive. However, one can cite as non-limiting examples solvents such as dipropyleneglycol, diethyl phthalate, isopropyl myristate, benzyl benzoate, 2-(2-ethoxyethoxy)-1-ethanol or ethyl citrate, which are the most commonly used. For the compositions which comprise both a perfumery carrier and a perfumery base, other suitable perfumery carriers than those previously specified, can be also ethanol, water/ethanol mixtures, limonene or other terpenes, isoparaffins such as those known under the trademark Isopar® (origin: Exxon Chemical) or glycol ethers and glycol ether esters such as those known under the trademark Dowanol® (origin: Dow Chemical Company).

As solid carriers one may cite, as non-limiting examples, absorbing gums or polymers, or yet encapsulating materials. Examples of such materials may comprise wall-forming and plasticizing materials, such as mono, di- or trisaccharides, natural or modified starches, hydrocolloids, cellulose derivatives, polyvinyl acetates, polyvinylalcohols, proteins or pectins, or yet the materials cited in reference texts such as H. Scherz, Hydrokolloide: Stabilisatoren, Dickungs- and Geliermittel in Lebensmitteln, Band 2 der Schriftenreihe Lebensmittelchemie, Lebensmittelqualitat, Behr's Verlag GmbH & Co., Hamburg, 1996. The encapsulation is a well known process to a person skilled in the art, and may be performed, for instance, using techniques such as spray-drying, agglomeration or yet extrusion; or consists of a coating encapsulation, including coacervation and complex coacervation technique.

By "perfumery base" we mean here a composition comprising at least one perfuming co-ingredient.

Said perfuming co-ingredient is not of formula (I). Moreover, by "perfuming co-ingredient" it is meant here a compound, which is used in a perfuming preparation or a composition to impart a hedonic effect. In other words such a co-ingredient, to be considered as being a perfuming one, must be recognized by a person skilled in the art as to being able to impart or modify in a positive or pleasant way the odor of a composition, and not just as having an odor.

The nature and type of the perfuming co-ingredients present in the base do not warrant a more detailed description here, which in any case would not be exhaustive, the skilled person being able to select them on the basis of his general knowledge and according to intended use or application and the desired organoleptic effect. In general terms, these perfuming co-ingredients belong to chemical classes as varied as alcohols, lactones, aldehydes, ketones, esters, ethers, acetates, nitriles, terpenoids, nitrogenous or sulphurous heterocyclic compounds and essential oils, and said perfuming co-ingredients can be of natural or synthetic origin. Many of these co-ingredients are in any case listed in reference texts such as the book by S. Arctander, Perfume and Flavor Chemicals, 1969, Montclair, N.J., USA, or its more recent versions, or in other works of a similar nature, as well as in the abundant patent literature in the field of perfumery. It is also understood that said co-ingredients may also be compounds known to release in a controlled manner various types of perfuming compounds.

By "perfumery adjuvant" we mean here an ingredient capable of imparting additional added benefit such as a color, a particular light resistance, chemical stability, etc. A detailed description of the nature and type of adjuvant commonly used in perfuming bases cannot be exhaustive, but it has to be mentioned that said ingredients are well known to a person skilled in the art.

An invention's composition consisting of at least one compound of formula (I) and at least one perfumery carrier represents a particular embodiment of the invention as well as a perfuming composition comprising at least one compound of formula (I), at least one perfumery carrier, at least one perfumery base, and optionally at least one perfumery adjuvant.

It is useful to mention here that the possibility to have, in the compositions mentioned above, more than one compound of formula (I) is important as it enables the perfumer to prepare accords, perfumes, possessing the odor tonality of various compounds of the invention, creating thus new tools for his work.

For the sake of clarity, it is also understood that any mixture resulting directly from a chemical synthesis, e.g. a reaction medium without an adequate purification, in which the compound of the invention would be involved as a starting, intermediate or to end-product could not be considered as a perfuming composition according to the invention as far as said mixture does not provide the invention's compound in a suitable form for perfumery.

Furthermore, the invention's compound can also be advantageously used in all the fields of modern perfumery, i.e. fine or functional perfumery, to positively impart or modify the odor of a consumer product into which said compound (I) is added.

Consequently, a perfuming consumer product which comprises:
i) as perfuming ingredient, at least one compound of formula (I), as defined above; and
ii) a perfumery consumer base;
is also an object of the present invention.

The invention's compound can be added as such or as part of an invention's perfuming composition.

For the sake of clarity, it has to be mentioned that, by "perfuming consumer product" it is meant a consumer product which is expected to deliver at least a perfuming effect, in other words it is a perfumed consumer product. For the sake of clarity, it has to be mentioned that, by "perfumery consumer base" we mean here the functional formulation, as well as optionally additional benefit agents, corresponding to a consumer product which is compatible with perfuming ingredients and is expected to deliver a pleasant odor to the surface to which it is applied (e.g. skin, hair, textile, or home surface). In other words, a perfuming consumer product according to the invention comprises the functional formulation, as well as optionally additional benefit agents, corresponding to the desired consumer product, e.g. a detergent or an air freshener, and an olfactive effective amount of at least one invention's compound.

The nature and type of the constituents of the perfumery consumer base do not warrant a more detailed description here, which in any case would not be exhaustive, the skilled person being able to select them on the basis of his general knowledge and according to the nature and the desired effect of said product.

Non-limiting examples of suitable perfumery consumer base can be a perfume, such as a fine perfume, a cologne or an after-shave lotion; a fabric care product, such as a liquid or solid detergent, a fabric softener, a fabric refresher, an ironing water, a paper, or a bleach; a body-care product, such as a hair care product (e.g. a shampoo, a coloring preparation or a hair spray), a cosmetic preparation (e.g. a vanishing cream or a deodorant or antiperspirant), or a skin-care product (e.g. a perfumed soap, shower or bath mousse, oil or gel, or a hygiene product); an air care product, such as an air freshener or a "ready to use" powdered air freshener; or a home care product, such as a wipe, a dish detergent or hard-surface detergent.

Some of the above-mentioned consumer product bases may represent an aggressive medium for the invention's compound, so that it may be necessary to protect the latter from premature decomposition, for example by encapsulation or by chemically bounding it to another chemical which is suitable to release the invention's ingredient upon a suitable external stimulus, such as an enzyme, light, heat or a change of pH.

The proportions in which the compounds according to the invention can be incorporated into the various aforementioned articles or compositions vary within a wide range of values. These values are dependent on the nature of the article to be perfumed and on the desired organoleptic effect as well as the nature of the co-ingredients in a given base when the compounds according to the invention are mixed with perfuming co-ingredients, solvents or additives commonly used in the art.

For example, in the case of perfuming compositions, typical concentrations are in the order of 0.1% to 30% by weight, or even more, of the compounds of the invention based on the weight of the composition into which they are incorporated. Concentrations lower than these, such as in the order of 0.05% to 15% by weight, can be used when these compounds are incorporated into perfumed articles, percentage being relative to the weight of the article.

The invention's compounds can be prepared according to a method as described in the Examples.

EXAMPLES

The invention will now be described in further detail by way of the following examples, wherein the abbreviations have the usual meaning in the art, the temperatures are indicated in degrees centigrade (° C.); the NMR spectral data were recorded in $CDCl_3$ (if not stated otherwise) with a 360 or 400 MHz machine for $^1H$ and $^{13}C$, the chemical shifts δ are indicated in ppm with respect to TMS as standard, the coupling constants J are expressed in Hz.

Example 1

Synthesis of Compounds of Formula (I)

1) (E)-4-methyl-5-(4-methylcyclohexyl)pent-4-enal a): 4-Methylcyclohexane carboxaldehyde (18 g, 111 mmol) was added dropwise to a 0.5 molar solution of isopropenylmagnesium bromide in THF (334 ml; 167 mmol), at −78° C. under nitrogen over a 1 hour period. The reaction was then slowly warmed up to room temperature. After cooling into an ice-water bath, aqueous saturated ammonium chloride (400 ml) was added (slowly until the exothermic reaction had subsided). After warming up to room temperature, the phases were separated. The aqueous phase was extracted with diethyl ether (500 ml). Each organic phase was washed with brine (300 ml). Combined extracts were dried over anhydrous sodium sulfate. The crude product was purified by column chromatography on silica gel (eluent: n-heptane/ethyl acetate 5:1) to give 15.66 g of product as a 2:3 mixture of diastereoisomers (91 mmol; 82%). It was further purified by bulb-to-bulb distillation (80° C./1 mbar).

$^1$H-NMR: 4.90-4.82 (m, 2H); 3.95 (broad d, J=7 Hz, 0.6H); 3.71 (broad d, J=7 Hz, 0.4H); 2.00-1.20 (m, 10H); 1.72 (s, 3H); 1.08-0.90 (m, 1H); 0.93 (d, J=7 Hz, 1.8H); 0.87 (d, J=7 Hz, 1.2H).

b): The alcohol obtained under part a) (14.18 g; 84 mmol), 3,6,912-tetraoxatetradeca-1,13-diene (19.8 g; 96 mmol), mercuric acetate (1.2 g, 3.8 mmol) and BHT (50 mg) were heated together in an oil bath at 140° C. overnight. After cooling to room temperature, the product was purified by column chromatography on silica gel (eluent: n-heptane/ethyl acetate 25:1) followed by bulb-to-bulb distillation (81° C./0.001 mbar).

6.1 g of the desired aldehyde were obtained (95% pure; 30 mmol; 36%) as a mixture of 4 isomers.

$^1$H-NMR: 9.79-9.72 (m, 1H); 5.32-4.95 (m, 1H); 2.53-2.25 (m, 4H); 2.10-1.20 (m, 9H); 1.62 (s, 3H); 1.08-0.92 (m, 1H); 0.90-0.85 (m, 3H).

2) (E)-5-cyclohexyl-4-methylpent-4-enal a): Cyclohexane carboxaldehyde (75 g; 649 mmol) was added neat to a 0.5 molar solution of isopropenyl magnesium bromide in THF (1200 ml; 600 mmol), while cooling in an ice bath, in order to keep the temperature below 10° C. The cooling bath was removed and, to after 1 hour, the reaction was heated to 45° C. or 30 minutes. The reaction was then cooled in an ice-water bath. A saturated aqueous ammonium chloride solution (1 liter) was added. The reaction was warmed up to room temperature and the mixture shaken vigorously. The phases were separated. The organic phase was washed with more ammonium chloride solution (500 ml) and brine (500 ml). Each aqueous phase was re-extracted with diethyl ether (500 ml). Combined extracts were dried over sodium sulfate. The product was purified by column chromatography on silica gel (eluent: n-heptane/ethyl acetate 5:1). A product of 95% chemical purity was obtained. It was further purified by fractional distillation under vacuum, to deliver the intermediate allylic alcohol with 77% yield. B.p.=37° C./0.008 mbar.

$^{13}$C-NMR: 146.52 (s); 112.28 (t); 80.97 (d); 40.52 (d); 29.66 (t); 28.47 (t); 26.50 (t); 26.26 (t); 26.05 (t); 17.40 (q).

$^1$H-NMR: 4.85 (m, 2H); 3.72 (m, 1H); 1.94 (m, 1H); 1.80-1.60 (m, 3H); 1.75 (broad s, 1H); 1.70 (s, 3H); 1.52-1.38 (m, 2H); 1.29-1.07 (m, 3H); 1.01-0.90 (m, 2H).

b): The alcohol obtained in part 1) (25 g; 162 mmol), 3,6,9,12-tetraoxatetradeca-1,13-diene (20.07 g; 97 mmol), mercuric acetate (1.6 g, 4.9 mmol) and BHT (100 mg) were heated together in an oil bath at 140° C. overnight. After cooling to room temperature, the product was purified by column chromatography on silica gel (eluent: n-heptane/ethyl acetate 22:1) followed by bulb-to-bulb distillation (60° C./0.001 mbar).

The desired aldehyde was obtained as a colorless liquid (100% pure; 12 g; 66.6 mmol; 41%) as a 4:1 E/Z mixture.

$^{13}$C-NMR (E-isomer): 202.65 (d); 132.08 (d); 131.05 (s); 42.40 (t); 36.94 (d); 33.24 (t); 31.88 (t); 26.11 (t); 26.04 (t); 16.18 (q).

$^1$H-NMR: 9.78 (m, 0.2H); 9.75 (m, 0.8H); 5.03-4.98 (m, 1H); 2.50 (m, 2H); 2.38-2.26 (m, 2H); 2.20-2.10 (m, 1H); 1.72-1.52 (m, 5H); 1.63 (s, 3H); 1.32-0.95 (m, 5H).

3) (E)-5-cyclohexyl-2,4-dimethylpent-4-enal

The alcohol obtained in part 2a (1; 38.84 g; 224 mmol); triethylortho propionate (102 g; 560 mmol), 2-ethylhexanoic acid (0.97 g; 6.7 mmol) and BHT (200 mg) in toluene (65 ml) were heated in an autoclave (purged with nitrogen) placed in an oil bath at 200° C. for 24 hours. After cooling to room temperature, the reaction was diluted with THF (300 ml) and poured onto a water solution of paratoluene sulfonic acid monohydrate (9 g to in 500 ml). After stirring for 5 minutes, solid sodium bicarbonate (6 g) was cautiously added portion wise. The phases were separated. The organic phase was washed with a saturated aqueous sodium bicarbonate solution (300 ml), water (1 liter) and brine (300 ml). Each aqueous phase was re-extracted with diethyl ether (300 ml). Combined extracts were dried onto solid anhydrous sodium sulfate. The product was concentrated onto the rotavapor. The product was dissolved in dry THF (200 ml) and added over a 2-hour period to a slurry of lithium aluminum hydride (95%, 12.7 g; 318 mmol) in dry THF (800 ml), under ice-water cooling.

The cooling bath was then removed and the reaction stirred overnight. After cooling in an ice-water bath, the reaction was treated successively with water (13 ml), 5% aqueous sodium hydroxide (39 ml) and water (13 ml). After warming up to room temperature, the reaction was stirred until a slurry was obtained (15 minutes). Solid anhydrous sodium sulfate (50 g) was added to the reaction, which was stirred for an additional 15 minutes. The solid was then filtered off, rinsed thoroughly with diethyl ether. The filtrate was concentrated on the rotavapor. The product was purified by bulb-to-bulb distillation (100-120° C./0.006 mbar).

The alcohol corresponding to the desired aldehyde was obtained as a colorless liquid, with an overall yield of 79%.

Without further purification of this alcohol (87 mmol), anhydrous sodium acetate (25 g) and BHT (200 mg) were slurred under nitrogen in dry dichloromethane (400 ml). The slurry was cooled into an ice-water bath and PCC (28.7 g; 130 mmol) was added in one portion. The reaction was warmed up to room temperature overnight by stirring and keeping the flask in the bath and allowing the ice to melt. Then diethyl ether (1 liter) was added. After stirring for 10 minutes, the reaction was passed through a short pad of silica gel (rinsing with diethyl ether). The product was purified by column chromatography on silica gel (eluent: n-heptane/ethyl acetate 25:1) followed by bulb-to-bulb distillation (61° C./0.009 mbar).

The desired aldehyde was obtained as a colorless oil with a yield of 39%.

$^{13}$C-NMR: 205.23 (d); 134.23 (d); 129.35 (s); 44.37 (d); 40.88 (t); 37.07 (d); 33.27 (t); 33.18 (t); 26.11 (t); 26.03 (t); 26.01 (t); 15.97 (q); 13.02 (q).

$^1$H-NMR: 9.60 (d, J=2 Hz, 1H); 5.02 (m, 1H); 2.54-2.43 (m, 1H); 2.39 (m, 1H); 2.21-2.09 (m, 1H); 1.95 (m, 1H); 1.72-1.53 (m, 5H); 1.61 (s, 3H); 1.32-1.10 (m, 3H); 1.07-0.97 (m, 2H); 1.02 (d, J=7 Hz, 3H).

4) 2,4-dimethyl-5-(4-methylcyclohexyl) pentanal

(E)-ethyl 2,4-dimethyl-5-(4-methylcyclohexyl)pent-4-enoate

The alcohol obtained in part 1a (32 g, 190 mmol), triethylortho propionate (76.7 g, 426 mmol), 2-ethylhexanoic acid (0.73 g, 5.1 mmol) and BHT (200 mg) in toluene (50 ml) were heated in an autoclave (purged with nitrogen) placed in an oil bath at 200° C. for 24 hours. After cooling to room temperature, the reaction was diluted with THF (300 ml) and poured onto a water solution of para-toluene sulfonic acid monohydrate (9 g in 500 ml). After stiffing for 5 minutes, solid sodium bicarbonate (6 g) was added portion wise and cautiously. The phases were separated. The organic phase was washed with a saturated aqueous sodium bicarbonate solution (300 ml), water (1 liter) and brine (300 ml). Each aqueous phase was re-extracted with diethyl ether (300 ml). Combined extracts were dried onto solid anhydrous sodium sulfate.

The product was purified by bulb-to-bulb distillation (107° C./0.1 mbar) and the product was obtained as a colorless liquid and a 56:44 mixture of diastereoisomers (42.9 g, yield 93%).

$^1$H-NMR: 5.27 (m, 0.5H); 4.95 (m, 0.5H); 4.10 (m, 2H); 2.58 (m, 1H); 2.40-2.30 (m, 1.5H); 2.10-1.96 (m, 1.5H); 1.70-1.37 (m, 5H); 1.61 (s, 3H); 1.25 (m, 5H); 1.12-0.85 (m, 8H).

(E)-2,4-dimethyl-5-(4-methylcyclohexyl)pent-4-en-1-ol

The ester obtained in the previous step (43.4 g, 96% pure, 165 mmol) was dissolved in dry THF (50 ml) and added over 1 hour to a slurry of lithium aluminum hydride (6.6 g, 165 mmol) in dry THF (950 ml), under ice-water cooling. The cooling bath was removed, the reaction stirred for 5 hours before being re-cooled into the ice-water bath. Water (11 ml), 5% aqueous sodium hydroxide (33 ml) and again water (11 ml) were successively added dropwise to the reaction. The cooling bath was removed and the reaction mixture stirred until a slurry was obtained (15 minutes). Solid anhydrous sodium sulfate (100 g) was added. After stirring for 15 minutes, the solid was filtered off, thoroughly rinsed with diethyl ether. The filtrate was concentrated on the rotavapor and the product purified by bulb-to-bulb distillation (100° C./0.057 mbar). The product was obtained with 94% yield and as a 1:1 mixture of diastereoisomers (E-isomers).

$^1$H-NMR: 5.28 (m, 0.5H); 4.97 (m, 0.5H); 3.52-3.37 (m, 2H); 2.40 (m, 0.5H); 2.10-2.00 (m, 1.5H); 1.90-1.40 (m, 8H); 1.61 (s, 3H); 1.32-1.20 (m, 2H); 1.10-0.82 (m, 8H).

(E)-2,4-dimethyl-5-(4-methylcyclohexyl)pent-4-enal

The alcohol obtained in part 2 (33.29 g, 158 mmol), and anhydrous sodium acetate (45 g) were slurred in dry dichlormethane (450 ml) and the reaction cooled into an ice-water bath. PCC (50 g, 227 mmol) was added portion wise to the reaction, which was stirred and slowly warmed up to room temperature overnight. Diethyl ether (1 liter) was added to the reaction. After 30 minutes the reaction was filtered through silica gel, rinsing with diethyl ether. The filtrate was concentrated on the rotavapor. The product was purified by column chromatography on silica gel (eluent: n-heptane/ethyl acetate 22:1) followed by bulb-to-bulb distillation (70° C./0.09 mbar). The product was obtained with a 52% yield and as a 1:1 mixture of diastereoisomers (E-isomers).

$^1$H-NMR: 9.62 (m, 1H); 5.30 (m, 0.5H); 4.98 (m, 0.5H); 2.52-1.90 (m, 4H); 1.70-1.20 (m, 7H); 1.61 (s, 3H); 1.10-0.85 (m, 8H).

2,4-dimethyl-5-(4-methylcyclohexyl)pentanal

The aldehyde obtained under part 3 (7.34 g, 35 mmol) was hydrogenated in presence of 5% palladium on carbon (0.15 g) in cyclohexane (30 ml) at room temperature and 20 bar $H_2$ until no more absorption could be seen. The product was purified by bulb-to-bulb distillation (61° C./0.074 mbar). The product was obtained with 93% yield and as a mixture of 4 diastereoisomers.

$^1$H-NMR: 9.61 (m, 1H); 2.45 (m, 1H); 1.72-1.40 (m, 7H); 1.33-1.20 (m, 4H); 1.18-0.94 (m, 5H); 0.94-0.78 (m, 8H).

5) 5-(bicyclo[2.2.1]heptan-2-yl)-4-methylpent-4-enal 1-(bicyclo[2.2.1]heptan-2-yl)-2-methylprop-2-en-1-ol Bicyclo[2.2.1]heptane-2-carbaldehyde (47 g, 378 mmol) in THF (25 ml) was added dropwise to isopropenylmagnesium bromide (0.5 molar in THF, 860 ml, 430 mmol) at −78° C. (slurry at this temperature) under nitrogen over 2 hours. The reaction was slowly warmed up to room temperature and stirred over the week-end. After cooling into an ice-water bath, a saturated aqueous ammonium chloride solution (500 ml) was added (slowly early on) to the reaction. The phases were vigorously stirred and separated. The organic phase was washed with more ammonium chloride solution (300 ml) and brine (300 ml). Each aqueous phase was re-extracted with diethyl ether (300 ml). Combined extracts were dried over sodium sulfate. The product was purified by fractional distillation through a 20-cm Widmer column.

The product was obtained with a yield of 91% and as a colorless liquid and a 68:32 mixture of diastereoisomers. B.p.=59° C./0.007 mbar.

$^1$H-NMR: 4.85 (m, 2H); 3.72-3.57 (m, 1H); 2.40-1.90 (m, 2H); 1.72-0.95 (m, 13H).

5-(bicyclo[2.2.1]heptan-2-yl)-4-methylpent-4-enal

The alcohol obtained under part 1 (25 g, 143 mmol), 3,6,9,12-tetraoxatetradeca-1,13-diene (35.4 g, 171 mmol), mercuric acetate (2.76 g, 8.6 mmol) and BHT (0.14 g) were heated together in an oil bath at 100-105° C. overnight. 40 ml of a mixture consisting of 63.64% acetic acid, 18.18% water and 18.18% sodium acetate were added to the reaction, which was heated under nitrogen in an oil bath at 115-120° C. for 2 hours. After cooling to room temperature, the reaction was poured onto water (500 ml) and extracted with diethyl ether (2×300 ml). Each organic phase was successively washed with water (twice), aqueous saturated bicarbonate (twice), water and brine (500 ml each). Combined extracts were dried over sodium sulfate. The product was purified by column chromatography on silica gel (eluent: heptane/ethyl acetate 25:1 to 15:1) followed by bulb-to-bulb distillation (70° C./0.002 mbar). The product was obtained with yield of 65% and a ratio 86:14 E/Z mixture.

$^{13}$C-NMR (E-isomer): 202.62 (d); 132.97 (d); 130.73 (s); 43.07 (d); 42.22 (t); 40.50 (d); 39.50 (t); 36.46 (d); 35.95 (t); 31.83 (t); 29.73 (t); 28.94 (t); 16.44 (q).

$^1$H-NMR: 9.72 (m, 1H); 5.05 (m, 1H); 2.50 (m, 2H); 2.38-2.16 (m, 4H); 1.92 (m, 1H); 1.61 (s, 3H); 1.58-1.08 (m, 8H).

6) 5-cyclohexyl-2,4-dimethylpentanal (E)-5-cyclohexyl-2,4-dimethylpent-4-enal (2.18 g; 11 mmol) was hydrogenated at 20 bar and room temperature in cyclohexane (20 ml) in the presence of 5% w/w palladium on charcoal (0.18 g). The thus obtained crude product was dissolved in dry dichloromethane (20 ml) and added drop-wise to a mixture of anhydrous sodium acetate (5 g) and finely ground pyridinium chlorochromate (PCC; 4.84 g; 22 mmol) in dry dichloromethane (50 ml) at 0° C. under nitrogen. The reaction was then stirred for 2 hours at room temperature. Diethyl ether (400 ml) was added to the reaction. After stirring for 30 minutes, the reaction was filtered through a short pad of silica gel, rinsing with diethyl ether. The product was purified by column chromatography on silica gel (eluent: heptanes/ethyl acetate 20:1) followed by bulb-to-bulb distillation (60° C./0.1 mbar). The product was obtained with a yield of 51% as a mixture of diastereoisomers.

$^1$H-NMR: 9.60 (m, 1H); 2.50-2.38 (m, 1H); 1.73-1.55 (m, 6H); 1.40-1.00 (m, 11H); 1.00-0.75 (m, 5H).

7) 4-methyl-5-(4-methylcyclohexyl)pentanal (E)-4-Methyl-5-(4-methylcyclohexyl)pent-4-enal (2.94 g; 15.13 mmol) was hydrogenated in cyclohexane (20 ml) at 20 bar and room temperature in the presence of 5% w/w palladium on charcoal (0.15 g). The product was purified by column chromatography on silica gel (eluent: heptanes/ethyl acetate 15:1) followed by bulb-to-bulb distillation (60° C./0.01 mbar).

The product was obtained as a colorless liquid and a 2:3 mixture of diastereoisomers (1.75 g; 8.8 mmol, 58%).

$^1$H-NMR: 9.76 (m, 1H); 2.50-2.35 (m, 2H); 2.70-2.60 (m, 3H); 1.60-1.35 (m, 6H); 1.32-1.20 (m, 4H); 1.15-1.00 (m, 2H); 0.92-0.80 (m, 6H).

8) 5-((1RS,4SR)-bicyclo[2.2.1]heptan-2-yl)-2,4-dimethylpent-4-enal 1-(Bicyclo[2.2.1]heptan-2-yl)-2-methylprop-2-en-1-ol (14.51 g; 83 mmol); 1-ethoxyprop-1-ene (E/Z mixture; 18.41 g; 207 mmol) and 85% phosphoric acid (90 mg, 0.78 mmol) were heated together in an autoclave (purged with nitrogen) placed in an oil bath at 120-125° C. for 6 hours (magnetic stirring). After cooling to room temperature, triethylamine (1 ml) was added and the mixture was directly purified by column chromatography on silica gel (eluent: heptanes/ethyl acetate 25:1) followed by bulb-to-bulb distillation (70° C./0.001 mbar).

The product was obtained as a colorless liquid and an 88:12 mixture of E and Z isomers (5.3 g; 26 mmol; 31%).

$^1$H-NMR: 9.60 (m, 1H); 5.10 (m, 1H); 2.50 (m, 1H); 2.38 (m, 1H); 2.20 (m, 2H); 2.00-1.90 (m, 2H); 1.62 (s, 3H); 1.60-1.10 (m, 8H); 1.05 (m, 3H).

9) 4-(cyclohexylmethylene)-2-methylhexanal a): 1-cyclohexyl-2-methylenebutan-1-ol 2-Ethylacroleine (25 g, 267 mmol) was added drop-wise to a 2 molar solution of cyclohexylmagnesium chloride in diethyl ether (167 ml, 334 mmol), at 0° C. under nitrogen. The reaction was then warmed up slowly to room temperature overnight. After cooling to 0° C., saturated aqueous NH$_4$Cl (500 ml) was added slowly. The reaction was warmed up to room temperature and phases separated. The aqueous phase was re-extracted with diethyl ether. Each organic phase was washed with brine. Combined extracts were dried over sodium sulfate. The product was purified by column chromatography on silica gel (eluent: heptanes/ethyl acetate 5:1) followed by bulb-to-bulb distillation (90-100° C./1 mbar). The product was obtained as colorless liquid (yield: 60%).

$^{13}$C-NMR: 152.39 (s); 109.61 (t); 80.85 (d); 40.99 (d); 29.88 (t); 28.34 (t); 26.52 (t); 26.31 (t); 26.10 (t); 23.64 (t); 12.10 (q).

$^1$H-NMR: 5.05 (m, 1H); 4.96 (m, 1H); 3.78 (d, J=7 Hz, 1H); 2.18-2.07 (m, 1H); 2.02-1.88 (m, 2H); 1.80-1.62 (m, 4H); 1.52-1.40 (m, 2H); 1.28-1.10 (m, 3H); 1.07 (t, J=7 Hz, 3H); 1.02-0.92 (m, 2H).

b): (E)-ethyl 4-(cyclohexylmethylene)-2-methylhexanoate

The following reagents were mixed and transferred into a stainless steel autoclave: above obtained alcohol (15.96 g; 94 mmol); triethyl orthopropionate (42.2 g; 235 mmol); 2-ethylhexanoic acid (0.68 g; 4.7 mmol) and toluene (50 ml). The autoclave was purged with nitrogen and heated in an oil bath at 195-200° C. overnight. After cooling to room temperature, the product was diluted with diethyl ether (200 ml). The solution was poured onto water (300 ml). 5% aqueous HCl (5 ml) was added and the mixture was stirred for 10 minutes. The phases were separated. The aqueous phase was extracted with diethyl ether. Each organic phase was washed with saturated aqueous NaHCO$_3$ and brine. Combined extracts were dried over sodium sulfate. The product was purified by bulb-to-bulb distillation (90-100° C./0.004 mbar). The product was obtained with 92% yield (96:4 ratio of E and Z isomers).

$^{13}$C-NMR: 176.7 (s); 136.07 (s); 133.2 (d); 60.04 (t); 40.40 (t); 38.29 (d); 36.78 (d); 33.72 (t); 33.65 (t); 26.12 (t); 26.07 (t); 22.95 (t); 16.82 (q); 14.29 (q); 13.66 (q).

$^1$H-NMR: 4.95 (m, 1H); 4.10 (m, 2H); 2.57 (m, 1H); 2.35 (m, 1H); 2.20-2.10 (m, 1H); 2.08-1.92 (m, 3H); 1.72-1.52 (m, 5H); 1.30-0.95 (m, 5H); 1.22 (t, J=7 Hz, 3H); 1.10 (d, J=7 Hz, 3H); 0.96 (t, J=7 Hz, 3H).

c): E)-4-(cyclohexylmethylene)-2-methylhexan-1-ol

The ester obtained previously (22.15 g; 86 mmol) was dissolved in anhydrous THF (100 ml) and the thus obtained solution was added drop-wise, at 0° C. under nitrogen, to a slurry of lithium aluminum hydride (5.2 g; 130 mmol) in dry THF (200 ml). The reaction was then warmed up to room temperature and stirred for 1 hour. After cooling back to 0° C., water (5 ml), 5% aq. NaOH (15 ml) and water (5 ml) were successively cautiously added. The mixture was warmed up to RT and stirred for 10 minutes. Sodium sulfate (60 g) was added and the mixture stirred for 10 minutes. The solid was filtered off, rinsed thoroughly with diethyl ether. The filtrate was concentrated in vacuo. The product was purified by bulb-to-bulb distillation (90° C./0.004 mbar). A 97:3 ratio of E and Z isomers was obtained. The product was with a yield of 93%.

$^{13}$C-NMR: 137.58 (s); 132.80 (d); 68.62 (t); 41.02 (t); 36.77 (d); 33.82 (d); 33.77 (t); 33.74 (t); 26.13 (t); 26.09 (t); 23.00 (t); 16.82 (q); 13.71 (q).

$^1$H-NMR: 4.95 (d, J=9 Hz, 1H); 3.44 (m, 2H); 2.22-2.10 (m, 1H); 2.10-1.97 (m, 3H); 1.85-1.75 (m, 3H); 1.70-1.54 (m, 5H); 1.32-1.00 (m, 5H); 0.97 (t, J=7 Hz, 3H); 0.87 (d, J=7 Hz, 3H).

d): 4-(cyclohexylmethylene)-2-methylhexanal

Finely ground PCC (21.3 g; 97 mmol) was added to a mixture of the above obtained alcohol (16.3 g; 77 mmol) and celite (20 g) in dry dichloromethane (200 ml), under nitrogen, ice-water cooling and mechanical stirring, in small portions. The reaction was slowly warmed up to room temperature overnight. Then, diethyl ether (750 ml) was added and the mixture was stirred for 30 minutes, before being filtered through silica gel (rinsing with diethyl ether). The product was purified by column chromatography on silica gel (eluent: heptanes/ethyl acetate 25:1) followed by bulb-to-bulb distillation (80° C./0.005 mbar) with a 96:4 ratio of E and Z isomers. The product was obtained as a colorless liquid (yield: 43%).

$^{13}$C-NMR: 205.29 (d); 135.26 (s); 133.87 (d); 44.51 (d); 37.54 (t); 36.85 (d); 33.68 (t); 33.62 (t); 26.08 (t); 26.04 (t); 26.03 (t); 23.03 (t); 13.61 (q); 13.27 (q).

$^1$H.NMR: 9.60 (m, 1H); 4.97 (d, J=9 Hz, 1H); 2.52-2.40 (m, 2H); 2.22-2.12 (m, 1H); 2.10-1.90 (m, 3H); 1.72-1.53 (m, 5H); 1.32-0.95 (m, 5H); 1.04 (d, J=7 Hz, 3H); 1.00 (t, J=7 Hz, 3H).

10) 5-cyclopentyl-2,4-dimethylpent-4-enal a): 1-cyclopentyl-2-methylprop-2-en-1-ol Neat cyclopentylcarbaldehyde (50.1 g; 0.5 mol) was added drop-wise to a commercial solution of isopropenylmagnesium bromide 0.5 M in THF (800 ml; 0.4 mol), under nitrogen and ice-water cooling. During the addition (3 hours), the internal temperature never exceeded 8° C. The reaction was then warmed up to room temperature and stirred for 1 hour before being re-cooled into an ice-water bath. Aqueous saturated NH$_4$Cl (500 ml) was added. The reaction was warmed up to room temperature and transferred into a separating funnel. After shaking vigorously, the phases were separated. The organic phase was washed with aqueous sat. NaHCO$_3$ (500 ml) and brine (500 ml). Each aqueous phase was re-extracted with diethyl ether (300 ml). Combined extracts were dried over sodium sulfate. The product was purified by column chromatography on silica gel (eluent: heptanes/ethyl acetate 5:1) followed by high vacuum distillation through a 20 cm Widmer column (33° C./0.005 mbar). The product was obtained with 71% yield.

$^{13}$C-NMR: 147.34 (s); 112.01 (t); 80.89 (d); 43.24 (d); 29.23 (t); 29.19 (t); 25.72 (t); 25.62 (t); 17.21 (q).

$^1$H-NMR: 4.90 (broad s, 1H); 4.82 (broad s, 1H); 3.78 (d, J=9, 1H); 2.03 (m, 1H); 1.76-1.85 (m, 2H); 1.72 (s, 3H); 1.68-1.48 (m, 5H); 1.45-1.36 (m, 1H); 1.22-1.11 (m, 1H).

b: (E)-ethyl 5-cyclopentyl-2,4-dimethylpent-4-enoate

The following reagents: triethyl orthopropionate (82 g; 458 mmol); the above obtained alcohol (27 g; 193 mmol) and 2-ethylhexanoic acid (1.03 g; 7.1 mmol) (+50 mg BHT) were stirred in toluene (30 g) in a stainless steel autoclave (purged with nitrogen; magnetic stirring)) placed in an oil bath at 195-200° C. for 24 hours. After cooling to room temperature, the reaction was poured onto water (300 ml) to which 5% aqueous HCl (5 ml) had been added. After 30 minutes stirring, the mixture was extracted with diethyl ether (2×300 ml). Each organic phase was washed with aqueous saturated NaHCO$_3$, water and brine (500 ml each). Combined extracts were dried over sodium sulfate. The product was purified by bulb-to-bulb distillation (80-90° C./0.001 mbar). The product was obtained with 99% yield.

$^{13}$C-NMR: 176.65 (s); 132.97 (d); 130.70 (s); 60.06 (t); 44.10 (t); 38.93 (d); 38.09 (d); 33.65 (t); 33.58 (t); 25.32 (t); 16.63 (q); 15.94 (q); 14.30 (q).

$^1$H-NMR: 5.09 (m, 1H); 4.10 (q, J=7 Hz; 2H); 2.63-2.52 (m, 2H); 2.32 (m, 1H); 2.01 (m, 1H); 1.80-1.70 (m, 2H); 1.70-1.50 (m, 4H); 1.62 (s, 3H); 1.24 (t, J=7 Hz, 3H); 1.20-1.12 (m, 2H); 1.10 (d, J=7 Hz; 3H).

c): (E)-5-cyclopentyl-2,4-dimethylpent-4-en-1-ol

The above-obtained ester (42.5 g; 186 mmol) in dry THF (250 ml) was added over 1 hour to a slurry of lithium aluminum hydride (12 g; 300 mmol) in dry THF (500 ml), under nitrogen and ice-water cooling (internal temperature kept under 10° C. at all the time). The cooling bath was then removed and the reaction stirred for 2 hours. After cooling the reaction into an ice-water bath, water (12 ml) was added drop-wise, followed by 5% aq. NaOH (36 ml) and again water (12 ml). After warming to room temperature, solid sodium sulfate (100 g) was added to dry the medium. After stirring for 10 minutes, the solid was filtered off, thoroughly rinsed with diethyl ether. The filtrate was concentrated on the rotavapor. The product was purified by bulb-to-bulb distillation (80-90° C./0.001 mbar). The product was obtained with 98% yield.

$^{13}$C-NMR: 132.35 (d); 132.32 (s); 68.56 (t); 44.41 (t); 38.95 (d); 33.68 (t); 33.65 (d); 25.32 (t); 25.31 (t); 16.71 (q); 16.18 (q).

$^1$H-NMR: 5.10 (m, 1H); 3.45 (m, 2H); 2.61 (m, 1H); 2.05 (m, 1H); 1.90-1.72 (m, 5H); 1.70-1.48 (m, 4H); 1.62 (s, 3H); 1.22-1.11 (m, 2H); 0.87 (d, J=7 Hz, 3H).

d): 5-cyclopentyl-2,4-dimethylpent-4-enal

PCC (24 g; 111 mmol) was added to the above-obtained alcohol (14.12 g; 77 mmol) and sodium acetate (6.29 g; 77 mmol) in dry dichloromethane (300 ml), under nitrogen and ice-water cooling. The reaction was slowly warmed up to room temperature overnight. Diethyl ether (600 ml) was added and the mixture was stirred for 30 minutes, before being filtered through a short pad of silica gel (rinsing with diethyl ether). The filtrate was concentrated on the rotavapor and the residue chromatographed on silica gel (eluent: heptanes/ethyl acetate 25:1). It was further purified by bulb-to-bulb distillation (80° C./1 mbar). The product was obtained with 60% yield.

$^{13}$C-NMR: 205.22 (d); 133.59 (d); 129.88 (s); 44.40 (d); 40.87 (t); 38.96 (d); 33.65 (t); 33.57 (t); 25.32 (t); 16.11 (q); 13.08 (q).

$^1$H-NMR: 9.61 (m, 1H); 5.11 (m, 1H); 2.60 (m, 1H); 2.52 (m, 1H); 2.40 (m, 1H); 1.97 (m, 1H); 1.82-1.72 (m, 2H); 1.70-1.48 (m, 4H); 1.62 (s, 3H); 1.22-1.12 (m, 2H); 1.03 (d, J=7 Hz, 3H).

11) (E)-5-cyclohexyl-2-ethyl-4-methylpent-4-enal a): The following reagents were heated in toluene (30 ml) in a stainless steel autoclave (purged with nitrogen) in an oil bath at 195-200° C. for 24 hours: 1-cyclohexyl-2-methyl-prop-2-en-1-ol (31.47 g; 201 mmol); triethyl orthobutyrate (44 g; 208 mmol); 2-ethylhexanoic acid (1.5 g; 10.5 mmol). The reaction was cooled to room temperature, diluted with diethyl ether, shaken for 5 minutes with 1% aq. HCl. The phases were separated. The aqueous phase was re-extracted with diethyl ether. Each organic phase was washed with aqueous sat. NaHCO$_3$ and brine. Combined extracts were dried over sodium sulfate. The product was sufficiently pure and directly used as such in the next step. The above obtained crude ester was added drop-wise (over 2 hours) to a slurry of lithium aluminum hydride (11 g; 275 mmol) in THF (800 ml), under nitrogen and ice-water cooling. The cooling bath was removed and the reaction stirred until room temperature was reached (2 hours). The reaction was cooled into an ice-water bath, and water (11 ml); 5% aqueous NaOH (33 ml) and water (11 ml) were cautiously added. The reaction was warmed up to room temperature and stirred until a white slurry was obtained (30 min) Solid, anhydrous sodium sulfate (50 g) was added and the mixture was stirred for 15 minutes. The solid was filtered off, rinsed with diethyl ether. The filtrate was concentrated on the rotavapor. The ester thus obtained was purified by bulb-to-bulb distillation (90° C./0.004 mbar) and recovered with 95% yield for the 2 steps.

$^{13}$C-NMR: 133.02 (d); 132.35 (s); 65.80 (t); 42.40 (t); 39.88 (d); 37.00 (d); 33.34 (t); 33.27 (t); 26.14 (t); 26.07 (t); 23.83 (t); 16.10 (q); 11.30 (q).

$^1$H-NMR: 5.03 (m, 1H); 3.52 (m, 2H); 2.16 (m, 1H); 1.97 (m, 2H); 1.72-1.55 (m, 7H); 1.62 (s, 3H); 1.40-0.98 (m, 7H); 0.91 (t, J=7, 3H).

b): Finely ground PCC (16.64 g; 77 mmol) was added in one portion to a slurry of the above-prepared alcohol (8.12 g; 38.6 mmol) and celite (20 g) in dry dichloromethane (300 ml), under nitrogen and ice-water cooling. The reaction was then slowly warmed up to room temperature overnight. Diethyl ether (700 ml) was added and the mixture was stirred for 30 minutes, before being filtered through a short pad of silica gel (rinsing thoroughly with diethyl ether). The filtrate was concentrated on the rotavapor. The product was purified by column chromatography on silica gel (eluent: heptanes/ethyl acetate 25:1) followed by bulb-to-bulb distillation (80° C./0.3 mbar) and recovered with 65% yield.

$^{13}$C-NMR: 205.42 (d); 134.00 (d); 129.59 (s); 51.38 (d); 39.13 (t); 37.03 (d); 33.23 (t); 33.19 (t); 26.11; t); 26.02 (t); 26.01 (t); 21.75 (t); 16.12 (q); 11.49 (q).

$^{1}$H-NMR: 9.53 (d, J=3, 1H); 5.02 (m, 1H); 2.38.2.26 (m, 2H); 2.20-2.03 (m, 2H); 1.70-1.43 (m, 7H); 1.62 (s, 3H); 1.32-0.94 (m, 5H); 0.90 (t, J=7, 3H).

12) 5-((1RS,2RS,4SR)-bicyclo[2.2.1]heptan-2-yl)-4-methylpentanal 5-(Bicyclo[2.2.1]heptan-2-yl)-4-methylpent-4-enal (20.6 g; 107 mmol) was hydrogenated in ethyl acetate (70 ml) in the presence of 5% palladium on charcoal (1.4 g) at room temperature and 30 bars. The product was purified by column chromatography on silica gel (eluent: heptanes/ethyl acetate 9:1) followed by bulb-t-bulb distillation (100° C./0.25 mbar). The product was obtained as a 1:1 mixture of diastereoisomers in 65% yield.

$^{1}$H-NMR: 9.75 (m, 1H); 2.50-2.34 (m, 2H); 2.15 (m, 1H); 1.89 (m, 1H); 1.72-1.58 (m, 1H); 1.52-1.33 (m, 6H); 1.32-0.92 (m, 7H); 0.88 (d, J=7 Hz, 3H).

13) (E)-5-(cyclohex-3-enyl)-4-methylpent-4-enal 1-(cyclohex-3-enyl)-2-methylprop-2-en-1-ol Lithium (2.87 g; 413 mmol) was covered with dry diethyl ether (30 ml) under Argon. The reaction was cooled to −30° C. and a solution of 2-bromopropene (25 g; 207 mmol) in dry diethyl ether (30 ml) was added drop-wise in 45 minutes. The reaction was slowly warmed up to room temperature and stirred for 1 hour. Then, after re-cooling to −30° C., cyclohex-3-enecarcaldehyde (18.77 g; 165 mmol) in dry diethyl ether (90 ml) was added over 45 minutes. The reaction was warmed up to room temperature and stirred for 1 hour. It was then poured onto ice/aqueous saturated NH$_4$Cl, extracted twice with ether. Extracts were washed with brine. Combined extracts were dried over sodium sulfate. The product was purified by column chromatography on silica gel (eluent: heptanes/ethyl acetate 4:1) followed by bulb-to-bulb distillation (75° C./0.5 mbar). The product (yield: 96%) was obtained as a 45:55 mixture of diastereoisomers.

$^{1}$H-NMR: 5.72-5.60 (m, 2H); 4.95-4.85 (m, 2H); 3.88-3.78 (m, 1H); 2.22-2.00 (m, 3H); 1.92-1.53 (m, 4H); 1.75 (s, 3H); 1.32-1.22 (m, 1H).

(E)-ethyl 5-(cyclohex-3-enyl)-4-methylpent-4-enoate

The following reagents were charged in a stainless steel autoclave: above-obtained alcohol (9.5 g; 62.4 mmol); triethyl orthoacetate (23.14 g; 140 mmol); 2-ethylhexanoic acid (0.24 g; 1.7 mmol) and toluene (18 ml). The autoclave was purged with nitrogen and heated in an oil bath at 200° C. overnight. After cooling to room temperature, the reaction was poured onto water. A few drops of 5% aq. HCl were added. The mixture was extracted twice with diethyl ether. Each organic phase was washed with water, aqueous saturated NaHCO$_3$ and brine (3×). Combined extracts were dried over sodium sulfate. The product was purified by column chromatography on silica gel (eluent: heptanes/ethyl acetate 9:1) followed by bulb-to-bulb distillation (120° C./0.01 mbar). The product was obtained (yield: 79%) as a 98:2 mixture of E and Z isomers.

$^{13}$C-NMR: 173.42 (s); 132.26 (s); 130.87 (d); 126.90 (d); 126.38 (d); 60.21 (t); 34.73 (t); 33.35 (t); 32.66 (d); 31.69 (t); 28.92 (t); 24.82 (t); 16.01 (q); 14.29 (q).

$^{1}$H-NMR: 5.66 (broad s; 2H); 5.06 (m, 1H); 4.12 (q, J=7, 2H); 2.48-2.40 (m, 1H); 2.40 (m, 2H); 2.30 (m, 2H); 2.08-1.98 (m, 3H); 1.78-1.60 (m, 2H); 1.65 (s, 3H); 1.40-1.30 (m, 1H); 1.25 (t, J=7, 3H).

(E)-5-(cyclohex-3-enyl)-4-methylpent-4-en-1-ol

The ester obtained previously (10.4 g; 46.8 mmol) was dissolved in anhydrous THF (55 ml) and the thus obtained solution was added drop-wise, at 0° C. under nitrogen, to a slurry of lithium aluminum hydride (1.12 g; 28.1 mmol) in dry THF (20 ml). The reaction was then warmed up to room temperature and stirred for 1 hour. After cooling back to 0° C., water (1 ml), 5% aq. NaOH (3 ml) and water (1 ml) were successively cautiously added. The mixture was warmed up to RT and stirred for 10 minutes. Sodium sulfate (20 g) was added and the mixture stirred for 10 minutes. The solid was filtered off, rinsed thoroughly with diethyl ether. The filtrate was concentrated in vacuo. The product was purified by bulb-to-bulb distillation (130° C./0.01 mbar) and recovered (yield: 95%) as a 98:2 mixture of E and Z isomers.

$^{13}$C-NMR: 133.61 (s); 130.61 (d); 126.91 (d); 126.44 (d); 62.79 (t); 36.02 (t); 32.68 (d); 31.77 (t); 30.78 (t); 29.00 (t); 24.86 (t); 15.99 (q).

$^{1}$H-NMR: 5.66 (m, 2H); 5.08 (m, 1H); 3.62 (t, J=7, 2H); 2.50-2.40 (m, 1H); 2.10-2.00 (m, 5H); 1.80-1.60 (m, 5H); 1.65 (s, 3H); 1.42-1.30 (m, 1H).

(E)-5-(cyclohex-3-enyl)-4-methylpent-4-enal

PCC (12.81 g; 58.2 mmol) was added portion-wise, at 0° C. under nitrogen, to a mixture of the above obtained alcohol (7 g; 38.8 mmol) and celite (14 g) in dry dichloromethane (100 ml). The reaction was warmed up to room temperature and stirred for 1 hour. The mixture was filtered through a short pad of silica gel, thoroughly rinsing with diethyl ether. The product was purified by column chromatography on silica gel (eluent: heptanes/ethyl acetate 50:1) followed by bulb-to-bulb distillation (65° C./1 mbar). The product was obtained (yield: 63%) as a 97:3 mixture of E and Z isomers.

$^{13}$C-NMR: 202.51 (d); 131.91 (s); 131.15 (d); 126.89 (d); 126.30 (d); 42.18 (t); 32.68 (d); 31.86 (t); 31.65 (t); 28.89 (t); 24.78 (t); 16.18 (q).

$^{1}$H-NMR: 9.73 (m, 1H); 5.66 (s, 2H); 5.07 (m, 1H); 2.52 (m, 2H); 2.50-2.40 (m, 1H); 2.32 (m, 2H); 2.08-2.00 (m, 3H); 1.80-1.60 (m, 2H); 1.65 (s, 3H); 1.38-1.30 (m, 1H).

Example 2

Preparation of a Perfuming Composition

A perfuming composition for Eau de Cologne for man, of the woody, musky type, was prepared by admixing the following ingredients:

| Parts by weight | Ingredient |
| --- | --- |
| 10 | Benzyl acetate |
| 15 | Styrallyl acetate |
| 25 | Ethyl acetoacetate |

-continued

| Parts by weight | Ingredient |
|---|---|
| 5 | 10%* Aldehyde C 10 |
| 10 | 10%* Aldehyde C 12 |
| 35 | 10%* Cinnamic aldehyde |
| 80 | Ambrox® [1] |
| 5 | Methyl anthranilate |
| 10 | 10%* Ethyl 2-methyl-pentanoate |
| 100 | Bergamot essential oil |
| 100 | Ethoxymethyl-cyclododecyl ether |
| 5 | 10%* Ethyl butyrate |
| 5 | Cardamom essential oil |
| 35 | 10%* Cis-3-Hexenol |
| 100 | Coranol™ [2] |
| 30 | 10%* 1,3-Dimethyl-3-phenylbutyl acetate |
| 180 | Coumarine |
| 15 | Allyl (cyclohexyloxy)-acetate |
| 5 | Damascenone |
| 20 | 10%* Damascone Alpha |
| 50 | (1'R,E)-2-ethyl-4-(2',2',3'-trimethyl-3'-cyclopenten-1'-yl)-2-buten-1-ol |
| 250 | Dihydromyrcenol |
| 30 | 1,1-Dimethyl-2-phenylethyl butanoate |
| 5 | Firascone® [3] |
| 10 | 3-(4/2-Ethylphenyl)-2,2-dimethylpropanal |
| 100 | Florol® [4] |
| 450 | Habanolide® [5] |
| 200 | Hedione® [6] HC |
| 75 | 3-(1,3-Benzodioxol-5-yl)-2-methylpropanal |
| 20 | 10%* Allyl heptanoate |
| 100 | Iralia® [7] |
| 550 | Iso E® [8] Super |
| 20 | Phenoxy isobutyrate |
| 70 | 10%* 3-Hexenyl-methyl carbonate |
| 140 | Mandarin essential oil |
| 25 | 10%* Mint essential oil |
| 70 | 6,6-Dimethoxy-2,5,5-trimethyl-2-hexene |
| 20 | Nutmeg essential oil |
| 350 | Muscenone® [9] Delta |
| 20 | Trans-1-(2,2,6-trimethyl-1-cyclohexyl)-3-hexanol |
| 20 | Pink pepper essential oil |
| 40 | Cis-3-Hexenyl salicylate |
| 5 | 2,4-Dimethyl-3-cyclohexene-1-carbaldehyde |
| 20 | 10%* Gamma undecalactone |
| 90 | Vanilline |
| 30 | Verdox® [10] |
| 450 | 10%** 8,13:13,20-Diepoxy-15,16-dinorlabdane |
| 4000 | |

* in dipropyleneglycol
** in isopropyle myristate
[1] (-)-(8R)-8,12-epoxy-13,14,15,16-tetranorlabdane; origin: Firmenich SA, Geneva, Switzerland
[2] 4-cyclohexyl-2-methyl-2-butanol; origin: Firmenich SA, Geneva, Switzerland
[3] methyl trans-2,6,6-trimethyl-3-cyclohexene-1-carboxylate; origin: Firmenich SA, Geneva, Switzerland
[4] tetrahydro-2-isobutyl-4-methyl-4(2H)-pyranol; origin: Firmenich SA, Geneva, Switzerland
[5] pentadecenolide; origin: Firmenich SA, Geneva, Switzerland
[6] methyl cis-dihydrojasmonate; origin: Firmenich SA, Geneva, Switzerland
[7] mixture of methylionones isomers; origin: Firmenich SA, Geneva, Switzerland
[8] 1-(octahydro-2,3,8,8-tetramethyl-2-naphthalenyl)-1-ethanone; origin: International Flavors & Fragrances, USA
[9] 3-methyl-5-cyclopentadecen-1-one; origin: International Flavors & Fragrances, USA
[10] 2-tert-butyl-1-cyclohexyl acetate; origin: International Flavors & Fragrances, USA The addition of 200 parts by weight of (E)-5-cyclohexyl-2,4-dimethylpent-4-enal to the above-described composition imparted to the latter a floral connotation of the lily of the valley type, which was very different from the one imparted when other known ingredients (of the same olfactive family, such as hydroxycitronellal or 3-(4-tert-butylphenyl)-2-methylpropanal) were used. The note imparted by the invention's compound was much stronger, more white flower, less green and more soft.

Example 3

Preparation of a Perfuming Composition

A perfuming composition for a detergent was prepared by admixing the following ingredients:

| Parts by weight | Ingredient |
|---|---|
| 20 | Citronellyl acetate |
| 100 | Geranyl acetate |
| 100 | Neryl acetate |
| 10 | Prenyl acetate |
| 10 | Styrallyl acetate |
| 50 | Hexyl acetate |
| 10 | Aladinate® [1] |
| 20 | 10%* Aldehyde C 10 |
| 200 | Hexylcinnamic aldehyde |
| 40 | 10%* 9-Undecenal |
| 10 | 1-(3,3-Dimethyl-1-cyclohexyl)ethyl formate |
| 10 | Ethyl 2-methyl-pentanoate |
| 150 | Benzylacetone |
| 20 | Cashmeran® [2] |
| 40 | Cetalox® [3] |
| 30 | 10%* Cis-3-Hexenol |
| 40 | 10%* Cis-Jasmone |
| 50 | Lemon essential oil |
| 180 | Coranol™ [4] |
| 30 | Allyl(cyclohexyloxy)-acetate |
| 20 | Damascone Alpha |
| 40 | 10%* Ethyl 2-methylbutyrate |
| 60 | Gamma decalactone |
| 150 | Habanolide® [5] |
| 300 | Hedione® [6] |
| 150 | Iso E® [7] Super |
| 400 | Linalool |
| 50 | Lyral® [8] |
| 10 | Crystal Moss |
| 10 | Myroxyde® [9] |
| 10 | 10%* Neobutenone® [10] Alpha |
| 20 | Nirvanol® [11] |
| 50 | Peonile® [12] |
| 50 | Phenethylol |
| 50 | Phenylhexanol |
| 300 | Romandolide® [13] |
| 170 | Benzyl salicylate |
| 100 | Cis-3-Hexenyl salicylate |
| 100 | Salicynile® [14] |
| 120 | Terpineol |
| 100 | Terpinolene |
| 20 | 2,4-Dimethyl-3-cyclohexene-1-carbaldehyde |
| 20 | Gamma undecalactone |
| 80 | Verdox® [15] |
| 3500 | |

* in dipropyleneglycol
[1] 3-methyl-2-hexenyl acetate; origin: Firmenich SA, Geneva, Switzerland
[2] 1,2,3,5,6,7-hexahydro-1,1,2,3,3-pentamethyl-4-indenone; origin: International Flavors & Fragrances, USA
[3] dodecahydro-3a,6,6,9a-tetramethyl-naphtho[2,1-b]furan; origin: International Flavors & Fragrances, USA
[4] 4-cyclohexyl-2-methyl-2-butanol; origin: Firmenich SA, Geneva, Switzerland
[5] pentadecenolide; origin: Firmenich SA, Geneva, Switzerland
[6] methyl dihydrojasmonate; origin: Firmenich SA, Geneva, Switzerland
[7] 1-(octahydro-2,3,8,8-tetramethyl-2-naphthalenyl)-1-ethanone; origin: International Flavors & Fragrances, USA
[8] 4/3-(4-hydroxy-4-methylpentyl)-3-cyclohexene-1-carbaldehyde; origin: International Flavors & Fragrances, USA
[9] 6,7-epoxy-3,7-dimethyl-1,3-octadiene; origin: Firmenich SA, Geneva, Switzerland
[10] 1-(5,5-dimethyl-1-cyclohexen-1-yl)-4-penten-1-one; origin: Firmenich SA, Geneva, Switzerland
[11] 3,3-dimethyl-5-(2,2,3-trimethyl-3-cyclopenten-1-yl)-4-penten-2-ol; origin: Firmenich SA, Geneva, Switzerland
[12] cyclohexylidene(phenyl)acetonitrile; origin: Givaudan SA, Vernier, Switzerland
[13] (1S,1'R)-[1-(3',3'-Dimethyl-1'-cyclohexyl)ethoxycarbonyl]methyl propanoate; origin: Firmenich SA, Geneva, Switzerland
[14] (2Z)-2-phenyl-2-hexenenitrile; origin: Firmenich SA, Geneva, Switzerland
[15] 2-tert-butyl-1-cyclohexyl acetate; origin: International Flavors & Fragrances, USA The addition of 500 parts by weight of (E)-5-cyclohexyl-2,4-dimethylpent-4-enal to the above-described composition imparted to the latter a clear, clean and very powerful lily of the valley, white flower connotation devoid of green, plastic aspect typical of other known ingredient (of the same olfactive family, such as 3-(4-tert-butylphenyl)-2-methylpropanal, 3-(4-isopropylphenyl)-2-methylpropanal, 3-(4-tert-butylphenyl)propanal or 3-(3-isopropyl-1-phenyl)butanal).

What is claimed is:

1. A compound of formula (I):

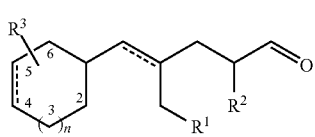

(I)

in the form of any one of its stereoisomers or a mixture thereof,
wherein each dotted line, independently from each other, represents a single or double bond;
n is 0 or 1;
$R^1$ represents a hydrogen atom or a methyl group;
$R^2$ represents a hydrogen atom or a methyl or ethyl group; and
$R^3$, which is a substituent in any of the positions 2 to 6 of the cyclic moiety, represents a hydrogen atom or a methyl or ethyl group, or a $CH_2$ group bridging position 3 and 6.

2. A compound according to claim 1, wherein the compound is of formula (II)

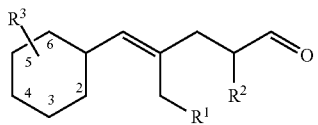

(II)

wherein $R^1$ represents a hydrogen atom or a methyl group;
$R^2$ represents a hydrogen atom or a methyl or ethyl group; and
$R^3$ represents a hydrogen atom or a methyl group, or a $CH_2$ group bridging positions 3 and 6 of the cyclic moiety;
provided that at least one of $R^2$ and $R^3$ is a hydrogen atom.

3. A compound according to claim 1, in the form of a mixture of isomers having a E/Z ratio of at least 80/20.

4. A compound according to claim 1, which is (E)-5-cyclohexyl-2,4-dimethylpent-4-enal, (E)-5-cyclohexyl-4-methylpent-4-enal, 5-((1RS,2RS,4SR)-bicyclo[2.2.1]heptan-2-yl)-4-methylpentanal, 5-((1RS,4SR)-bicyclo[2.2.1]heptan-2-yl)-2,4-dimethylpent-4-enal or 5-cyclohexyl-2,4-dimethylpentanal.

5. A perfuming composition comprising
i) at least one compound of formula (I), as defined in claim 1;
ii) at least one ingredient selected from the group consisting of a perfumery carrier and a perfumery base; and
iii) optionally at least one perfumery adjuvant.

6. A perfuming consumer product comprising:
i) at least one compound of formula (I), as defined in claim 1; and
ii) a perfumery consumer base.

7. A perfuming consumer product according to claim 6, wherein the perfumery consumer base is a perfume, a fabric care product, a body-care product, an air care product or a home care product.

8. A perfuming consumer product according to claim 6, wherein the perfumery consumer base is a fine perfume, a cologne, an after-shave lotion, a liquid or solid detergent, a fabric softener, a fabric refresher, an ironing water, a paper, a bleach, a shampoo, a coloring preparation, a hair spray, a vanishing cream, a deodorant or antiperspirant, a perfumed soap, shower or bath mousse, oil or gel, a hygiene product, an air freshener, a "ready to use" powdered air freshener, a wipe, a dish detergent or hard-surface detergent.

9. A method to impart aldehyde, lily of the valley odor notes to a composition or product, which comprises providing in a perfuming composition or perfuming consumer article a fragrance effective amount of a compound according to claim 1.

10. The method according to claim 9, compound is of formula (II)

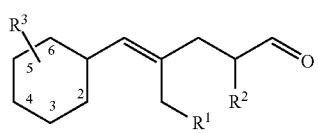

(II)

wherein $R^1$ represents a hydrogen atom or a methyl group;
$R^2$ represents a hydrogen atom or a methyl or ethyl group; and
$R^3$ represents a hydrogen atom or a methyl group, or a $CH_2$ group bridging positions 3 and 6 of the cyclic moiety;
provided that at least one of $R^2$ and $R^3$ is a hydrogen atom.

11. The method according to claim 9 wherein the compound is in the form of a mixture of isomers having a E/Z ratio of at least 80/20.

12. The method according to claim 9 wherein the compound is (E)-5-cyclohexyl-2,4-dimethylpent-4-enal, (E)-5-cyclohexyl-4-methylpent-4-enal, 5-((1RS,2RS,4SR)-bicyclo[2.2.1]heptan-2-yl)-4-methylpentanal, 5-((1RS,4SR)-bicyclo[2.2.1]heptan-2-yl)-2,4-dimethylpent-4-enal or 5-cyclohexyl-2,4-dimethylpentanal.

13. The method according to claim 9, wherein the compound is present in a perfuming composition that also includes at least one ingredient selected from the group consisting of a perfumery carrier and a perfumery base; and optionally at least one perfumery adjuvant.

14. The method according to claim 9, wherein the compound is present in consumer product that includes a perfumery consumer base.

15. The method according to claim 14, wherein the perfumery consumer base is a perfume, a fabric care product, a body-care product, an air care product or a home care product.

16. The method according to claim 14, wherein the perfumery consumer base is a fine perfume, a cologne, an after-shave lotion, a liquid or solid detergent, a fabric softener, a fabric refresher, an ironing water, a paper, a bleach, a shampoo, a coloring preparation, a hair spray, a vanishing cream, a deodorant or antiperspirant, a perfumed soap, shower or bath mousse, oil or gel, a hygiene product, an air freshener, a "ready to use" powdered air freshener, a wipe, a dish detergent or hard-surface detergent.

* * * * *